(12) United States Patent
Liu et al.

(10) Patent No.: US 7,508,521 B2
(45) Date of Patent: Mar. 24, 2009

(54) PRESSURE-INVARIANT TRACE GAS DETECTION

(75) Inventors: Xiang Liu, Phoenix, AZ (US); Xin Zhou, Racho Cucamonga, CA (US); Alfred Feitisch, Los Gatos, CA (US); Greg Sanger, Chico, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 50 days.

(21) Appl. No.: 11/724,665

(22) Filed: Mar. 14, 2007

(65) Prior Publication Data

US 2008/0225296 A1 Sep. 18, 2008

(51) Int. Cl.
G01N 21/00 (2006.01)
G01N 7/00 (2006.01)
G01N 9/00 (2006.01)
G01N 19/00 (2006.01)
G01N 25/00 (2006.01)
G01N 27/00 (2006.01)

(52) U.S. Cl. .................. 356/437; 356/432; 73/23.27

(58) Field of Classification Search ......... 250/230–232; 356/432–444; 372/26, 33–38.09, 55
See application file for complete search history.

(56) References Cited

U.S. PATENT DOCUMENTS

| | | | | |
|---|---|---|---|---|
| 2,690,695 | A | * | 10/1954 | Coates ..................... 356/246 |
| 3,614,243 | A | * | 10/1971 | Harvey ..................... 356/246 |
| 3,723,731 | A | * | 3/1973 | Blau, Jr. .................. 356/451 |
| 3,810,695 | A | * | 5/1974 | Shea ........................ 356/73 |
| 4,829,183 | A | | 5/1989 | McClatchie |
| 4,953,390 | A | | 9/1990 | Krempl |
| 5,026,991 | A | | 6/1991 | Goldstein |
| 5,107,118 | A | | 4/1992 | Murray et al. |
| 5,268,736 | A | * | 12/1993 | Prather ..................... 356/246 |
| 5,528,040 | A | | 6/1996 | Lehmann |

(Continued)

FOREIGN PATENT DOCUMENTS

DE 3413914 A1 10/1985

(Continued)

OTHER PUBLICATIONS

Bomse, Davis S. et al., "Frequency modulation and wavelength modulation spectroscopes: comparison of experimental methods using a lead-salt diode laser", Applied Optics; 31(6): 718-731 (1992).

(Continued)

Primary Examiner—L. G Lauchman
Assistant Examiner—Jarreas C Underwood
(74) Attorney, Agent, or Firm—Mintz, Levin, Cohn, Ferris, Glovsky and Popeo, P.C.

(57) ABSTRACT

A system includes a light source, a detector, at least one pressure sensor, and a control unit. The light source emits light at a wavelength substantially corresponding to an absorption line of a target gas. The detector is positioned to detect the intensity of light emitted from the light source that has passed through the target gas. The pressure sensor detects the pressure of the target gas. The control circuit is coupled to the detector and the light source to adjust the modulation amplitude of the light source based on the pressure detected by the at least one pressure sensor. Related systems, apparatus, methods, and/or articles are also described.

30 Claims, 5 Drawing Sheets

U.S. PATENT DOCUMENTS

| | | | | |
|---|---|---|---|---|
| 5,572,031 | A | * | 11/1996 | Cooper et al. ............... 250/343 |
| 5,657,126 | A | * | 8/1997 | Ducharme et al. .......... 356/369 |
| 5,742,053 | A | * | 4/1998 | Rekunyk ................. 250/338.5 |
| 5,760,895 | A | | 6/1998 | Kebabian |
| 5,777,329 | A | | 7/1998 | Westphal et al. |
| 5,847,392 | A | | 12/1998 | Van Den Berg et al. |
| 5,880,850 | A | * | 3/1999 | McAndrew et al. ......... 356/437 |
| 5,958,340 | A | | 9/1999 | Meyer et al. |
| 5,963,336 | A | | 10/1999 | McAndrew |
| 6,064,488 | A | * | 5/2000 | Brand et al. ............... 356/440 |
| 6,188,475 | B1 | | 2/2001 | Inman et al. |
| 6,292,756 | B1 | | 9/2001 | Lievois et al. |
| 6,353,225 | B1 | | 3/2002 | Strzoda et al. |
| 6,420,695 | B1 | | 7/2002 | Grasdepot et al. |
| 6,519,039 | B1 | * | 2/2003 | Morishita et al. ........... 356/437 |
| 6,657,198 | B1 | * | 12/2003 | May ...................... 250/339.13 |
| 6,762,836 | B2 | | 7/2004 | Benicewicz et al. |
| 6,841,781 | B2 | | 1/2005 | Toomey |
| 7,116,422 | B2 | | 10/2006 | Larking et al. |
| 7,132,661 | B2 | | 11/2006 | May |
| 7,176,464 | B2 | * | 2/2007 | Oka et al. ................... 250/343 |
| 7,193,718 | B2 | | 3/2007 | Lundqvist et al. |
| 7,228,017 | B2 | | 6/2007 | Xia et al. |
| 2002/0190840 | A1 | | 12/2002 | Fujita et al. |
| 2003/0213912 | A1 | | 11/2003 | Tulip |
| 2004/0079887 | A1 | | 4/2004 | May |
| 2006/0163483 | A1 | | 7/2006 | Chabanis et al. |
| 2006/0176486 | A1 | | 8/2006 | Ho |
| 2006/0192967 | A1 | | 8/2006 | Kluczynski |

FOREIGN PATENT DOCUMENTS

| | | |
|---|---|---|
| EP | 0 768 523 A2 | 4/1997 |
| EP | 0922908 | 6/1999 |
| GB | 2416205 | 1/2006 |
| WO | WO03/100393 | 12/2003 |
| WO | WO2005/047872 | 5/2005 |

OTHER PUBLICATIONS

Brown, L.R. et al., "Experimental Line Parameters of the Oxygen A Band at 760 nm", Journal of Molecular Spectroscopy, 199: 166-179 (2000).

Cassidy, Daniel T. et al., "Atmospheric pressure monitoring of trace gases using tunable diode lasers", Applied Optics, 21(7): 1185-1190 (1982).

Cassidy, Daniel T. et al., "Trace gas detection with short-external-cavity InGaAsP diode laser transmitter modules operating at 1.58 μm", Applied Optics, 27(13): 2688-2693 (1988).

Herriott, Donald R. et al., "Folded Optical Delay Lines", Applied Optics, 4(8): 883-889 (1965).

Herriott, Donald R. et al., "Off-Axis Paths in Spherical Mirror Interferometers", Applied Optics, 3(4): 523-526 (1964).

"In-Situ Sensors for the Chemical Industry—Final Report", project report of "Development of In Situ Analysis for the Chemical Industry", the Dow Chemical Company, Principle investigator: Dr. J.D. Tate, profect No.: DE-FC36-o21D14428, pp. 1-37, Jun. 30, 2006.

Kessler, William J. et al., "Near-IR diode laser-based sensor for pb-level water vapor in industrial gases", Proceedings of the SPIE, 3537: 139-149 (1999).

May, Randy D. et al., "Data Processing and Calibration for Tunable Diode Laser Harmonic Absorption Spectrometers", Journal of Quantitative Spectroscopy and Radiative Transfer, 49(4): 335-347 (1993).

May, Randy D. et al., "Open-Path, Near-Infrared Tunable Diode Laser Spectrometer for Atmospheric Measurements of $H_2O$", Journal of Geophysical Research, 103:19161-19172 (1998).

May, Randy D., "Computer Processing of Tunable Diode Laser Spectra", Applied Spectroscopy, 43(5): 834-839 (1989).

May, Randy D., "Next-Generation Diode Laser Gas Sensors for Environmental and Industrial Monitoring", Proceedings of the SPIE, 3858: 110-118 (1999).

Paige, Mark E., "Commercial Gas Sensing with Vertical Cavity Lasers", Advanced Semiconductor Lasers and Their Applications Conference Technical Digest; pp. 141-143 (1999).

Philippe, Louis C. et al., "Laser diode wavelength-modulation spectroscopy for simultaneous measurement of temperature, pressure, and velocity in shock-heated oxygen flows", Applied Optics, 32(30): 6090-6103(1993).

Reid, J. et al., "Second-Harmonic Detection with Tunable Diode Lasers—Comparison of Experiment and Theory", Applied Physics, B 26: 203-210 (1981).

Richter, Dirk et al., "Development of an automated diode-laser-based multicomponent gas sensor", Applied Optics, 39(24): 4444-4450 (2000).

Rothman et al., "The HITRAN molecular spectroscopic database: edition of 2000 including updates through 2001", Journal of Quantitative Spectroscopy & Radiative Transfer, 82: 5-44 (2003).

Scott, David C. "Airborne Laser Infrared Absorption Spectrometer (ALIAS-II) for in situ atmospheric measurements of $N_2O$, $CH_4$, CO, HCL and $NO_2$ from balloon or remotely piloted aircraft platforms", Applied Optics, 38(21): 4609-4622 (1999).

Silver, Joel A., "Frequency-modulation spectroscopy for trace species detection: theory and comparison among experimental methods", Applied Optics, 31(6): 707-717 (1992).

Wang, Jian et al., "In situ combustion measurements of CO with diode-laser absorption near 2.3 μm", Applied Optics, 39(30): 5579-5589 (2000).

Webster, Christopher R. et al., Aircraft (ER-2_laser infrared absorption spectrometer (ALIAS) for in-situ stratospheric measurements of HCL $N_2O$, $CH_4$, $NO_2$, and $HNO_3$, Applied Optics, 33(3): 454-472 (1994).

Webster, Christopher R. et al., "Quantum-cascade laser measurements of stratospheric methane and nitrous oxide", Applied Optics, 40(3): 321-326 (2001).

Webster, Christopher R. et al., "Tunable diode laster IR spectrometer for in situ measurements of the gas phase composition and particle size distribution of Titan's atmosphere", Applied Optics, 29(7): 907-917 (1990).

Zhou, Xin et al., "Development of a sensor for temperature and water concentration in combustion gases using a single tunable diode laser", Measurement Science and Technology, 14: 1459-1468 (2003).

'The HITRAN Database', [online]. Harvard-Smithsonian Center for Astrophysics, 2006, [retrieved on May 8, 2007]. Retrieved from the Internet: <URL:www.cf.harvard.edu/hitran/welcometop.html>.

Allen, Mark G., "Diode laser absorption sensors for gas-dynamic and combustion flows", Meas. Sci. Technol.; 9:545-562 (1998).

May, Randy D. et al., "The MVACS tunable diode laser spectrometers", Journal of Geophysical Research, 106(E8): 17673-17682 (Aug. 25, 2001).

May, Randy D., "Correlation-based technique for automated tunable diode laser scan stabilization", Rev. Sci. Instrum.; 63(5): 2922-2926 (1992).

Silver, Joel A. et al., "Diode laser measurements of concentration and temperature in microgravity combustion", Meas. Sci. Technol, 10:845-852 (1999).

Webster, Christopher R. et al., "Simultaneous in Situ Measurements and Diurnal Variations of NO, $NO_2$, $O_3$, $jNO_2$, $CH_4$, $H_2O$, and $CO_2$ in the 40- to 26-km Region Using an Open Path Tunable Diode Laser Spectrometer", Journal of Geophysical Research, 92(D10): 11931-11950 (Oct. 20, 1987).

Inman, Ronald S., et al., "Application of Tunable Diode Laser Absorption Spectroscopy to Trace Moisture Measurements In Gases," Anal. Chem. 66. 2471-2479 (1994).

Mucha, J.A., et al., "Infrared Diode Laser Determination of Trace Moisture in Gases," ISA Transactions, vol. 25, No. 3, 25-30 (1986).

* cited by examiner

PRESSURE-INVARIANT TRACE GAS DETECTION

TECHNICAL FIELD

The subject matter described herein relates to pressure-invariant techniques for measuring concentrations of trace gases.

BACKGROUND

Industries such as the petrochemical industry often require precise measurements of trace gases within background gases to ensure that concentrations of such trace gases are within acceptable limits. Compliance with these limits in turn can be used to verify factors such as whether the delivered gases meet certain purity limits and/or whether emissions of such gases comply with environmental regulations. In some cases, optical sensors utilizing harmonic spectroscopy have been used to measure concentrations of trace gases. However, pressure variations in samples of gas delivered to optical sensors can distort second harmonic signals thereby resulting in inaccurate measurements.

SUMMARY

In one aspect, an apparatus includes a light source that emits light at a wavelength substantially corresponding to an absorption line of a target gas, a detector positioned to detect an intensity of light emitted from the light source that has passed through the target gas at a frequency at a multiple of a modulation frequency of the light source, at least one pressure sensor to detect a pressure associated with the target gas, and a control unit coupled to the detector and the light source to adjust a modulation amplitude of the light source based on the pressure detected by the at least one pressure sensor.

The light source may be, for example, a solid state laser, a tunable diode laser, a quantum cascade laser, a gas laser, a liquid laser, a color center laser, an optical difference or sum frequency generator, and the like. The detector may be, for example, an InGaAs detector, an InAs detector, a Si detector, a Ge detector, a PbS detector, a Mercury-Cadmium-Telluride detector, a photomultiplier, and the like. The pressure sensor may be, for example, a piezo-resistive pressure sensor, a strain gauge pressure sensor, a mechanical deflection pressure sensor, a vibrating element pressure sensor, a variable capacitance pressure sensor, and the like.

In some implementations, a sample cell is utilized to increase an effective path length of light emitted from the light source that is coupled to the light source and the detector. In such variations, one or more of the pressure sensors can be configured to measure pressure within the sample cell. The sample can be an open path sample cell to increase an effective path length of light emitted from the light source such as, for example, a Herriott cell, a White cell, a cell that has at least one surface reflecting the light emitted from the light source, a cell that has no surface reflecting the light emitted from the light source, and the like. The sample call can be a closed path cell to increase the effective path length of light emitted from the light source such as, for example, such as an on-axis optical resonator having at least one surface reflecting the light emitted from the light source, or an off-axis optical resonator having at least one surface reflecting the light emitted from the light source, and the like.

The control unit can be operable to vary the modulation of the light source according to changes in detected pressure. In some implementations, the shape of the light detected by the detector includes a peak and a valley and the control unit varies the modulation amplitude of the light source to maintain a substantially fixed distance between the peak and the valley, or to maximize a distance between the peak and the valley. The shape of the light may also comprise a peak so that the control unit either varies the modulation amplitude of the light source to maintain a substantially fixed height of the peak or to maximize a heat of the peak.

In an interrelated aspect, a trace concentration of a target gas within a background gas over a range of pressures can be detected by emitting modulated light at a wavelength substantially corresponding to at least one absorption line of the target gas, detecting an intensity of light emitted from the light source that has passed through the target gas at a multiple of a modulation frequency of the emitted light, detecting a pressure of the target gas, and adjusting a modulation amplitude of the modulated light based on the detected pressure of the target gas.

In still a further interrelated aspect, an apparatus includes a light source emitting light at a wavelength at which molecules of a target gas absorb light at a substantially greater level than molecules of a background gas, a detector positioned to detect an intensity of light emitted from the light source, at least one pressure sensor to detect a pressure associated with the target gas, and a control unit coupled to the detector and the light source to adjust an operating parameter of the light source based on the pressure detected by the at least one pressure sensor.

Articles are also described that comprise a tangibly embodied machine-readable medium embodying instructions that, when performed, cause one or more machines (e.g., computers, etc.) to result in operations described herein. Similarly, computer systems are also described that may include a processor and a memory coupled to the processor. The memory may encode one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
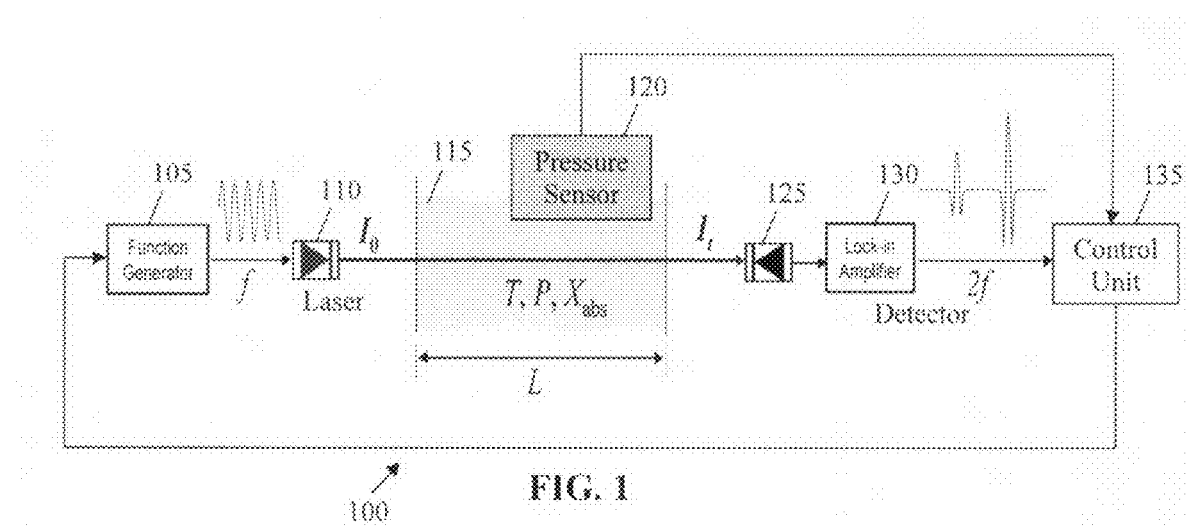
FIG. 1 is a schematic diagram of a system for measuring a concentration of a trace gas in a background gas at varying pressures.

FIG. 1 is a schematic diagram of an apparatus 100 for measuring trace amounts of a target gas within a background gas that may include a function generator 105, a laser 110 (or other light source such as a hot filament, a glow bar, color center laser, quantum cascade laser, an optical difference or sum frequency generator, or any suitable emitter in the corresponding wavelength region of interest, etc.), a sample cell 115 (or sample pathway), a pressure sensor 120 (e.g., a piezoresistive pressure sensor, a strain gauge pressure sensor, a mechanical deflection pressure sensor, a vibrating element pressure sensor, a variable capacitance pressure sensor, etc.), a detector 125 (an InGaAs detector, an InAs detector, a Si detector, a Ge detector, a PbS detector, a Mercury-Cadmium-Telluride detector, a photomultiplier, etc.), a lock-in amplifier 130, and a control unit 135. The function generator 105 is operable to adjust one or more operating parameters of the laser 110, such as modulation amplitude based on a level of signal detected by the detector 125 and locked in by the lock-in-amplifier 130 after a sample of gas has passed through the sample cell 115. The sample cell may comprise an open path (e.g., a Herriott cell, a White cell, a cell that has at least one surface reflecting the light emitted from the light source, a cell that has no surface reflecting the light emitted from the light source, etc.) or closed path (e.g., on-axis optical resonator having at least one surface reflecting the light emitted from the light source, or an off-axis optical resonator having at least one surface reflecting the light emitted from the light source, etc.) measurement system. The control unit 135 is operable to instruct the function generator 105 to modify one or more operating parameters of the laser 110 (e.g., modulation amplitude, etc.) based on the signal provided by the lock-in-amplifier 130 and/or based on a pressure level detected by the pressure sensor 120.

The laser 110 can comprise a tunable diode laser (TDL) and in such cases, tunable diode laser absorption spectroscopy (TDLAS) can be utilized as a non-intrusive, fast, sensitive and reliable solution for gas species detection in various flows. In particular, the function generator 105 can modulate the laser 110 and the detector 125 can detect the emitted light at a multiple of the modulation frequency of the laser 110 to provide wavelength modulation based TDLAS with second harmonic (2f) detection (WMS-2f) resulting in sensitive absorption spectroscopy measurements. Such an arrangement minimizes 1/f noise, and removes the sloping baseline that is present on TDL spectra (due to the fact that the laser output power increases as the laser injection current increases). However, as the WMS-2f signal strength is pressure dependent, the optimum Signal-to-Noise Ratio (SNR) usually can only be maintained for different pressures through adjustment of one or more operating parameters of the light source 100 by the function generator 105 as instructed by the control unit 135.

In some implementations, a pressure of the background gas is at least 1 Pa. In addition or in the alternative, the concentration of the trace gas can be at least 0.01 part per trillion volume of the background gas.

Figure 2:
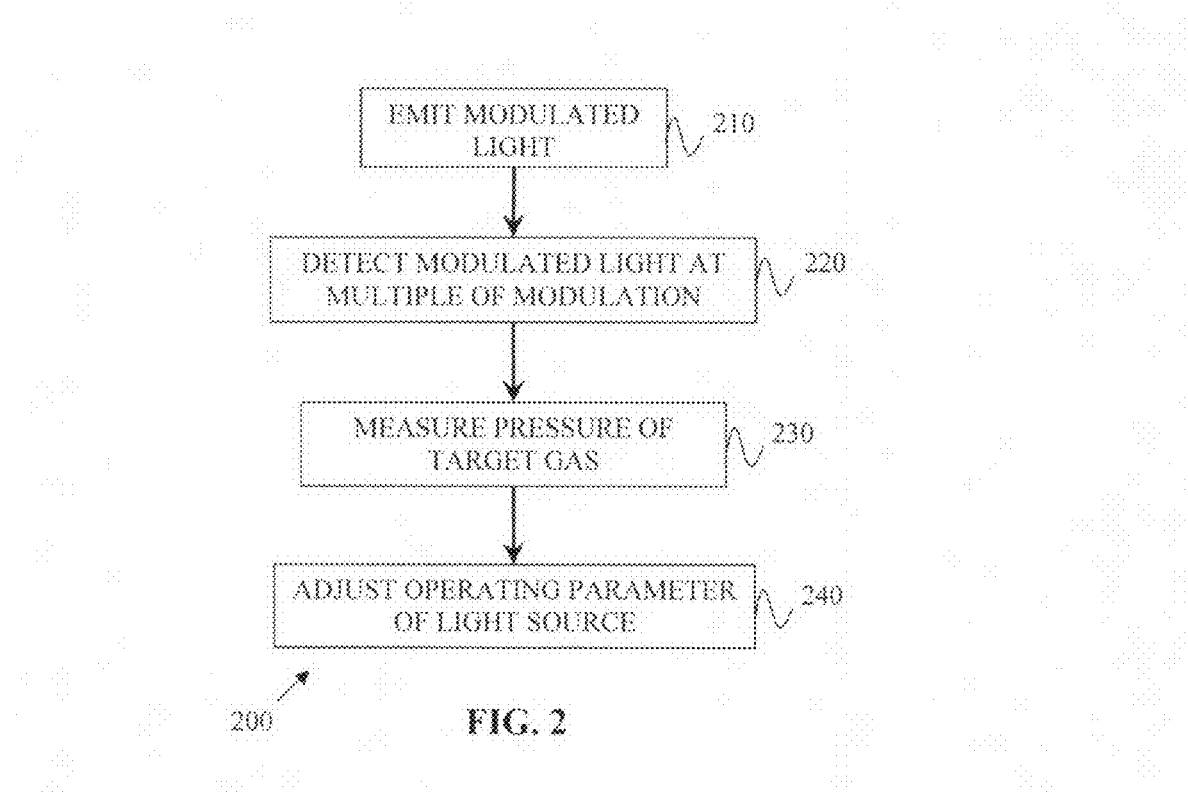
FIG. 2 is a process flow diagram illustrating a method of measuring a concentration of a trace gas in a background gas at varying pressures.

FIG. 2 is a process flow diagram illustrating a method 200 of detecting a trace concentration of a target gas within a background gas over a range of pressures in which, at 210, modulated light is emitted at a wavelength substantially corresponding to at least one absorption line of the target gas. The intensity of the emitted light is detected at a frequency equal to a multiple of the modulation frequency of a light source emitting the modulated light, at 220, after it has passed through the target gas. In addition, the pressure of the target gas is, at 230, detected. Thereafter, the modulation amplitude of the modulated light is adjusted, at 240, based on the detected pressure of the target gas.

In WMS-2f absorption measurements, the injection current of the laser 110 can be sinusoidally modulated by the function generator 105 at frequency f [Hz], the instantaneous laser frequency can be described by a linear frequency modulation (FM)

$$v(t) = \bar{v} + a\cos(\omega t), \quad (1.1)$$

where $\omega = 2\pi f$ is the angular frequency, $\bar{v}$ [cm$^{-1}$] is the center laser frequency and a [cm$^{-1}$] the FM amplitude. The transmitted laser intensity $I_t(t)$ is measured by the detector 125 after passing through the sample cell 115, and the lock-in amplifier 130 can be used to isolate the second harmonic component of the detected signal. The spectral absorbance $\alpha$ is defined using the incident ($I_0$) and transmitted ($I_t$) laser intensity $$\alpha = -\ln\left(\frac{I_t}{I_0}\right). \quad (1.2)$$

The detected WMS-2f signal at a given frequency $\bar{v}$ can be mathematically modeled as $$S_{2f} = \frac{G\bar{I}_0}{2}\left[H_2 - \frac{i_0}{2}(H_1 + H_3)\right], \quad (1.3)$$

where G is the optical-electronical gain of the detection system (e.g., detector 125 and lock-in amplifier 130), $\bar{I}_0$ is the average laser intensity at frequency $\bar{v}$, $i_0$ is the Intensity Modulation (IM) amplitude, and $H_k$ is the $k^{th}$ coefficient of the Fourier Cosine transformation of the spectral absorbance $$H_k(\bar{v}, a) = -\frac{PX_{abs}L}{\pi}\int_{-\pi}^{\pi}\sum_i (S(T)\phi(\bar{v} + a\cos(\omega t)))_i \cos(k\omega t) d(\omega t), \quad (1.4)$$

where P is the pressure and T is the temperature of the sample gas passing through the sample cell 115, $X_{abs}$ is the mole fraction of the absorbing species in the sample gas, L is the pathlength, S is the linestrength and $\phi$ is the lineshape function of the i$^{th}$ transition. The summation accounts for the absorption contributions from neighboring transitions, which may not be negligible at elevated pressures due to pressure broadening and blending. The lineshape function $\phi(v)$ of a particular absorption transition, which represents the relative variation in the spectral absorbance with frequency, is a function of the pressure P, the temperature T and the absorber mole fraction $X_{abs}$.

If the absorber mole fraction $X_{abs}$ is very small, the 2f signal can be regarded as proportional to $X_{abs}$ due to the negligible dependence of the lineshape functions $\phi(v)$ on $X_{abs}$. This linearity of the 2f signal versus $X_{abs}$ (within a limited range) has been demonstrated for trace gas detection in various applications. As shown in equation (1.4), 2f signal also exhibits nonlinear dependence on both temperature and pressure due to their effects on lineshape function. Pressure has much stronger effects on line shape function than temperature. The temperature dependence of 2f signal is usually weak and can be neglected for near-room temperature operations. However, the pressure-dependence of 2f signal cannot be omitted due to its strong effects on the final readings. For conventional WMS-2f based analyzers with fixed modulation amplitude, pressure calibration/correction is usually performed to compensate such pressure effects.

Figure 3A:
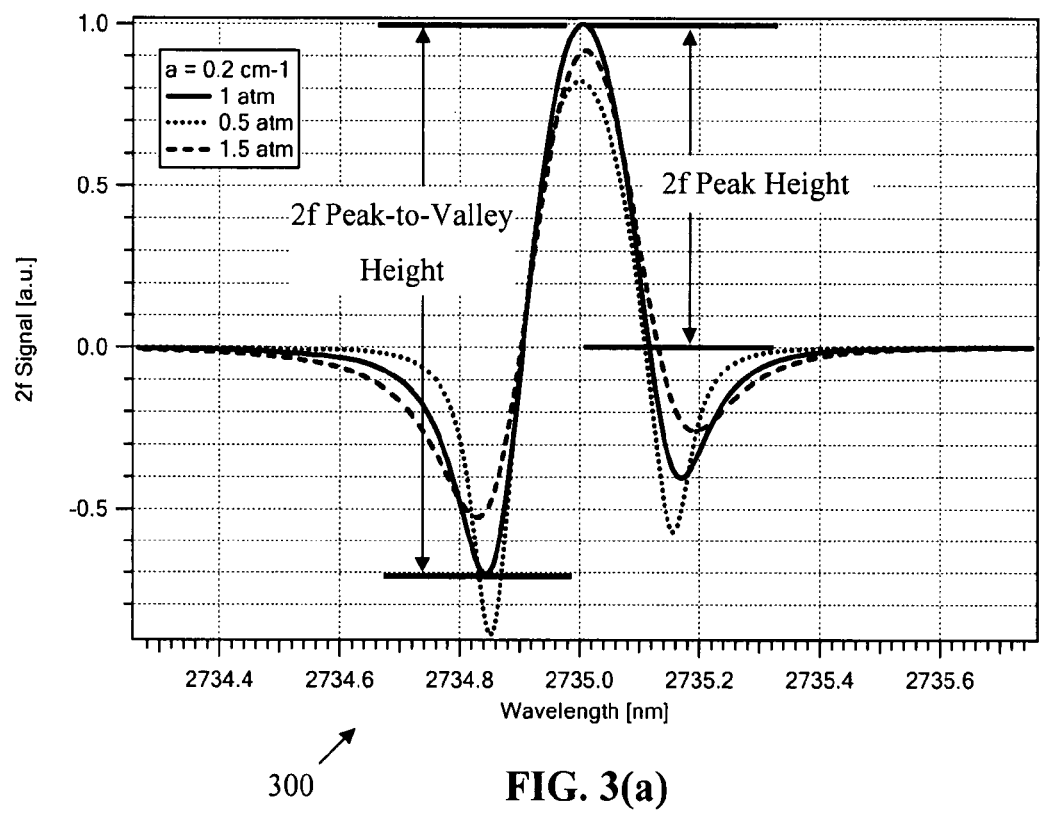
FIGS. 3(a)-3(b) are graphs illustrating pressure dependence of a detected signal in a system such as that illustrated in FIG. 1.

FIG. 3(a) is a graph 300 that illustrates the pressure-dependence of a WMS-2f spectra (a=0.2 cm$^{-1}$) at different pressures for a typical isolated $H_2O$ absorption transition. Here the 2f spectra of a typical isolated $H_2O$ absorption transition are simulated at various pressures between 0-3 atm using Eq. (1.3)-(1.4) and the HITRAN 2004 spectroscopic database. The 2f peak heights at different pressures can be inferred from the simulated spectra and plotted in the graph 350 of FIG. 3(b). As can be seen, with fixed modulation amplitude, the 2f peak height rises to a maximum and then drops when pressure increases. The pressure where the 2f peak height reaches the maximum is determined by the modulation amplitude.

For some conventional WMS-2f based TDLAS gas analyzers, the linear dependence of the 2f peak height on $X_{abs}$ is only calibrated at one nominal pressure (e.g. 1 atm). The constant modulation amplitude is usually selected to maximize the 2f peak height at the nominal pressure. But as can be seen from FIG. 3(b) which illustrates a variation of the 2f peak height with pressure at different "a" for the transition of FIG. 3(a), if the actual pressure of the sample gas deviates from the nominal pressure (e.g., in many industrial environments, the gas stream pressure varies with time), the 2f peak height (and thus the detection sensitivity) will deteriorate and the WMS-2f based analyzer will give faulty readings unless the pressure dependence has been calibrated in advance.

The current modulation amplitude of the laser 110 can be adjusted so that the FM amplitude "a" varies proportionally to the pressure $$a=K\cdot P, \quad (1.5)$$

where K is a constant. For convenience in the following discussions, K is expressed as the multiple of the pressure-broadening coefficient γ of the absorption transition $$K=C\gamma, \quad (1.6)$$

where C is a constant which can be determined by theory, or generally by simulation or experimental calibration.

Figure 4:
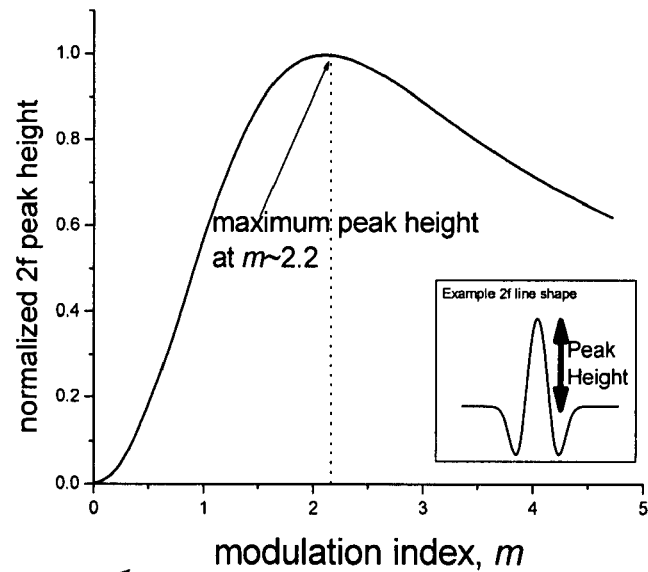
FIG. 4 is a graph illustrating a dependence of peak height on a modulation index of a light source.

In implementations in which the 2f peak height is used for the WMS-2f based gas sensing, for a well-isolated absorption transition, the constant C can be set at around 2.2. This value can be derived from the theory that for an isolated transition at a constant temperature T and absorber concentration $X_{abs}$, the 2f peak height is only dependent on the modulation index m, which is defined as $$m = \frac{a}{\Delta v} = \frac{a}{P\cdot\gamma}, \quad (1.7)$$

where Δv is the half width at half maximum of the absorption transition. The 2f peak height for any isolated absorption transition reaches its maximum at m≈2.2 for all line shapes, as illustrated in graph 400 of FIG. 4 which illustrates the dependence of WMS-2f peak height on modulation index m.

Therefore, in implementations in which the 2f peak height is used for the WMS-2f based gas sensing, for a well-isolated absorption transition, the FM amplitude "a" can be adjusted according to Eq. (1.5) and (1.6) with the constant C set at approximately 2.2, so that the 2f peak height can be maintained at the maximum under various pressures, as demonstrated by graph 500 of FIG. 5 which illustrates 2f peak height versus pressure for the isolated $H_2O$ absorption transition used in FIGS. 3(a)-(b) at fixed "a" and when adjusting "a" proportionally to pressure. This arrangement enables the WMS-2f based gas analyzer to maintain optimum detection sensitivity and accuracy at different pressures. Therefore the analyzer can be used in varying-pressure environments, instead of requiring a constant, low pressure to achieve sufficient detection sensitivity.

Figure 3B:
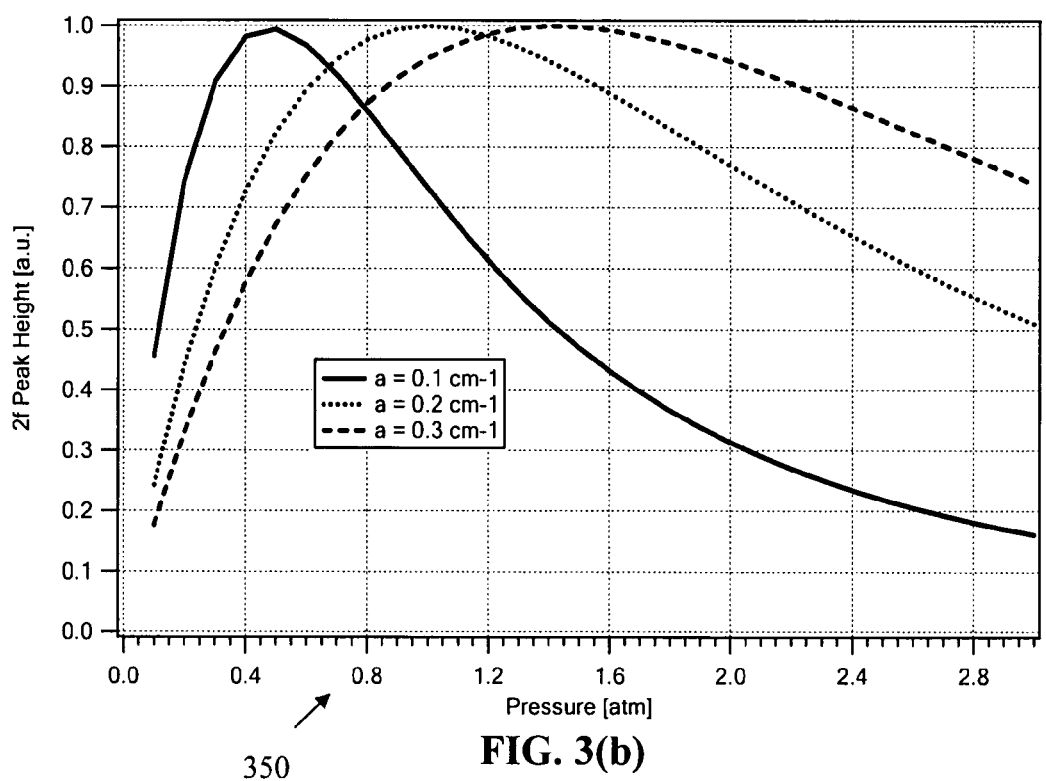
Figure 5:
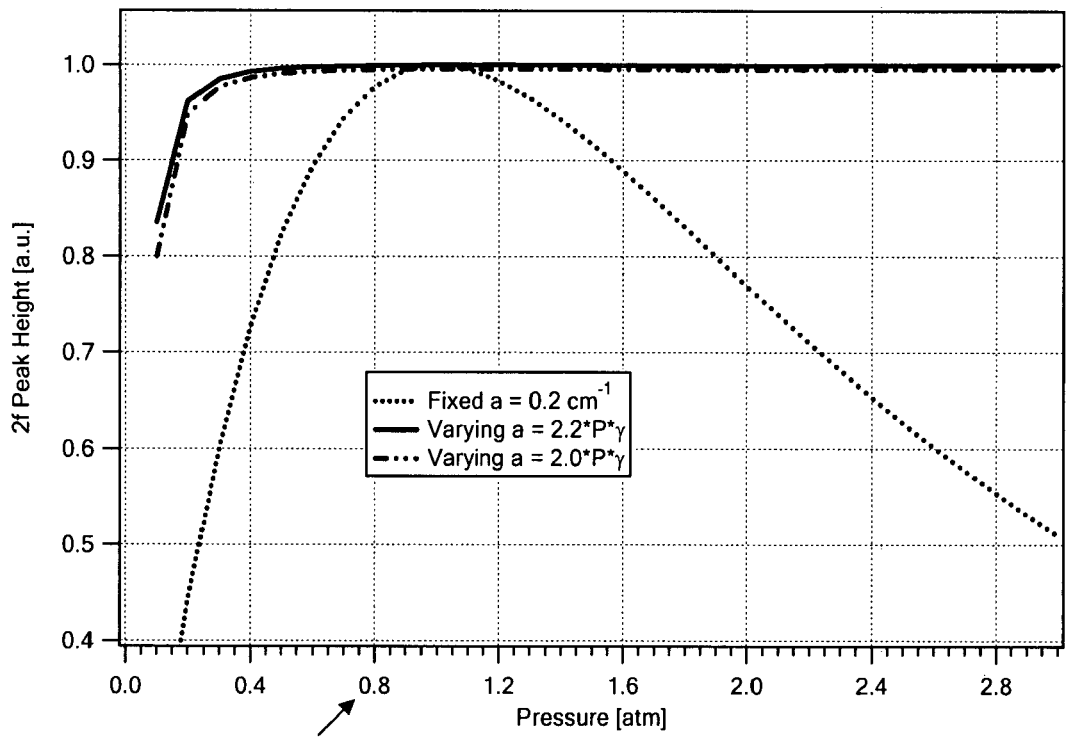
FIG. 5 is a graph illustrating second harmonic peak height versus pressure for an isolated absorption transition when adjusting the modulation amplitude proportionally to pressure compared with the case at a fixed modulation amplitude.

For a relatively isolated transition, the pressure-dependence of the 2f peak height can be largely eliminated, as illustrated in graph 500 of FIG. 5, because the maxima of the 2f peak heights at various pressures are almost constant for a wide range of pressures, as can be seen from FIGS. 3(a)-3(b). The removal of the pressure-dependence of the 2f peak height eliminates the necessity for the pressure-calibration of the analyzer, and helps to improve the sensor accuracy and performance, especially under varying-pressure environments.

Figure 6:
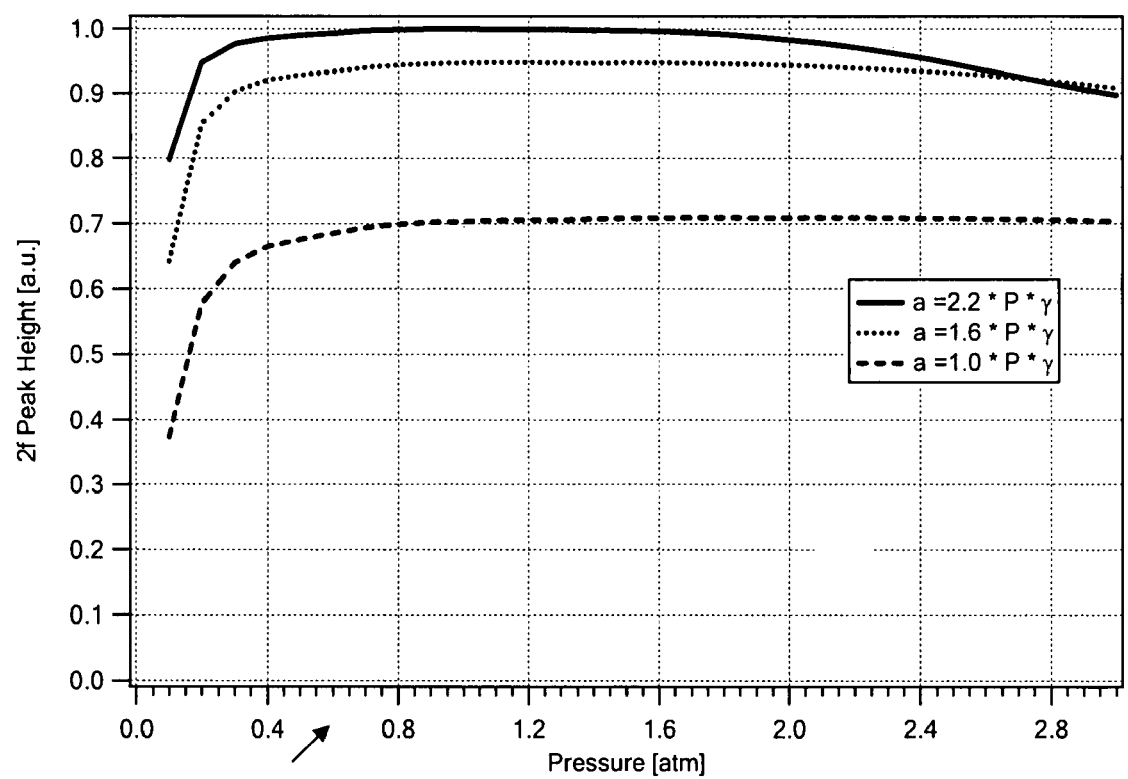
FIG. 6 is a graph illustrating second harmonic peak height versus pressure for a non-isolated absorption transition when adjusting a modulation amplitude proportionally to pressure.

In implementations in which the 2f peak height is used for the WMS-2f based gas sensing, if the target absorption transition is not well-isolated, the constant C can be set at a lower value than the optimum value of 2.2 in order to reduce the interferences from neighboring transitions by using smaller modulation amplitudes. By setting C<2.2, a flatter curve of 2f peak height versus pressure can be obtained at the price of a somewhat lower SNR, as shown in graph 600 of FIG. 6 (which illustrates 2f peak height versus pressure for a non-isolated $H_2O$ absorption transition at 1877.1 nm when adjusting "a" proportionally to pressure), thereby removing pressure dependence of 2f peak height for a wide range of pressures.

Figure 7:
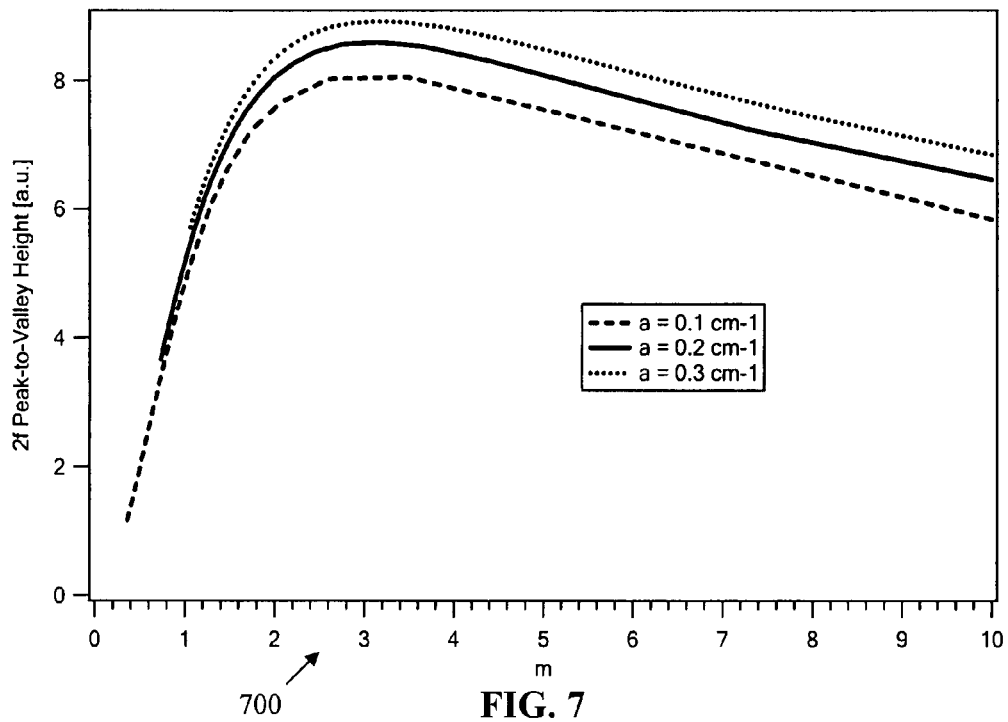
FIG. 7 is a graph illustrating a second harmonic peak-to-valley height versus modulation index at various fixed modulation amplitudes.
Figure 8:
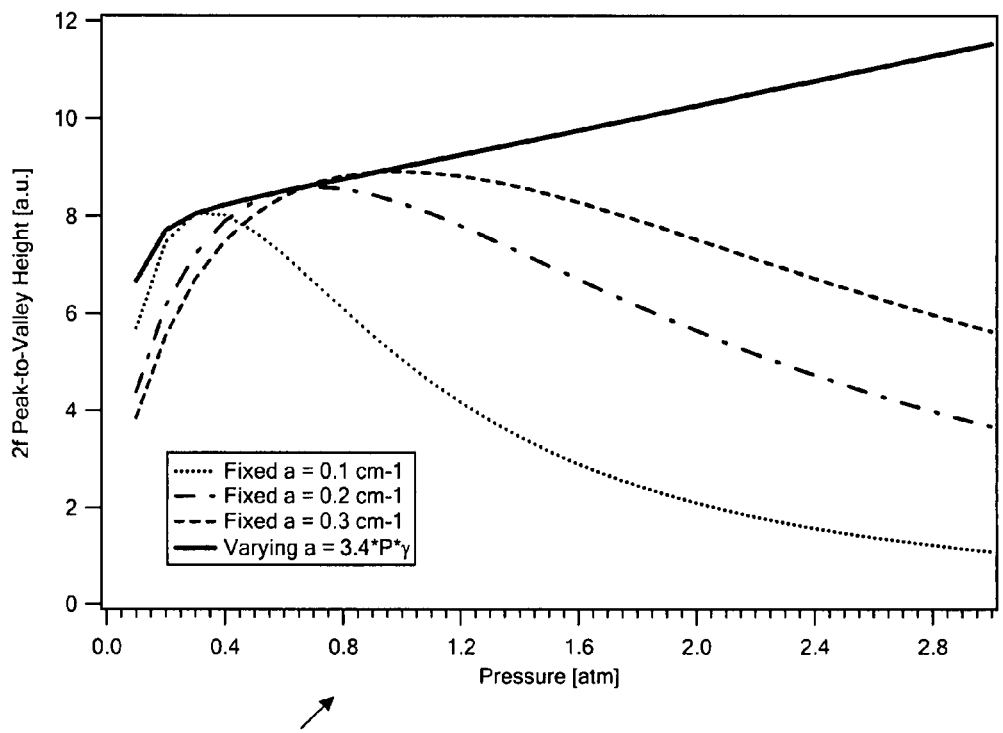
FIG. 8 is a graph illustrating a second harmonic peak-to-valley height versus pressure at various fixed modulation amplitudes and at a variable modulation amplitude.

In some implementations, rather than 2f peak height being utilized for WMS-2f based gas sensing, the 2f peak-to-valley height is used. In such variations, the constant C that achieves the maximum peak-to-valley heights at various pressures can be determined by simulations. As shown in graph 700 of FIG. 7, the 2f peak-to-valley heights simulated with different "a", at different pressures, are plotted against the modulation index m for the isolated $H_2O$ absorption transition used in FIGS. 3 and 5. The constant C can be taken as the optimum m that enables the maximum (or near maximum) 2f peak-to-valley heights for all the curves. In this illustrative example, the C value is about 3.3-3.4. Therefore, in the WMS-2f based trace gas analyzer, the FM amplitude "a" can be adjusted according to Eq. (1.5) and (1.6) with the constant C set at the desired value, so that the 2f peak-to-valley height (and thus the detection sensitivity) can be maintained at the maximum (or near maximum) under various pressures, as demonstrated in graph 800 of FIG. 8, which illustrates 2f peak-to-valley height versus pressure for the isolated $H_2O$ absorption transition used in FIG. 7 at fixed "a" and when adjusting "a" proportionally to pressure. Alternatively, the FM amplitude "a" can be adjusted as a nonlinear function of pressure so that the 2f peak-to-valley height is invariant for different pressures. Such a nonlinear correlation between the FM amplitude "a" and the pressure can be obtained from calibration experiments.

All the above illustrations are based, at least in part, on simulations using Eq. (1.3)-(1.4), where the IM (intensity modulation) of the laser is assumed to be linear and out-of-phase with the FM of the laser. Also, in all the simulations, the IM amplitude $i_0$ is approximated to be equal to the FM amplitude "a". In some variations, $i_0$ can be measured for different "a", and further calibration experiments can be conducted to verify the optimum value for the constant C. The pressure range within which the subject matter described herein can be employed will only be limited by the maximum achievable modulation amplitudes of the lasers, which may differ from device to device and are correlated to the modulation frequencies of the lasers. Maximum modulation amplitudes achievable by commercial TDLs can make the 2f peak height of well-isolated transitions invariant for practical stream pressures of 0.5 atm to >5 atm, which exceeds typical pressure variations found in the petrochemical applications.

The systems and techniques described herein provide many advantages. For example, by allowing a WMS-2f based TDLAS gas analyzer to maintain the optimum 2f signal, such an analyzer can maintain optimum detection sensitivity over a wide range of pressures. In addition, by significantly reducing pressure-dependence of a 2f signal, routine pressure calibration procedures for the conventional WMS-2f based gas analyzers can be simplified, and in some cases, eliminated.

Aspects of the subject matter described herein may be embodied in systems, apparatus, methods, and/or articles depending on the desired configuration. In particular, various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein do not require the particular order shown, or sequential order, to achieve desirable results. It will be appreciated that other light sources other than lasers may be utilized and/or that operating parameters other than modulation amplitude may be adjusted based on detected pressure levels. Other embodiments may be within the scope of the following claims.

What is claimed is:

1. An apparatus comprising;
    at least one light source emitting light at a wavelength substantially corresponding to an absorption line of a target gas;
    at least one detector positioned to detect an intensity of light emitted from the light source that has passed through the target gas at a frequency at a multiple of a modulation frequency of the light source;
    at least one pressure sensor to detect a pressure associated with the target gas; and
    a control unit coupled to the at least one detector and the at least one light source to automatically adjust a modulation amplitude of the light source based on the pressure detected by the at least one pressure sensor.

2. An apparatus as in claim 1, wherein the at least one light source is selected from a group comprising: a solid state laser, a tunable diode laser, a quantum cascade laser, a gas laser, a liquid laser, a color center laser, or an optical difference or sum frequency generator.

3. An apparatus as in claim 1, wherein the at least one detector is selected from a group comprising: an InGaAs detector, an InAs detector, a Si detector, a Ge detector, a PbS detector, a Mercury-Cadmium-Telluride detector, or a photomultiplier.

4. An apparatus as in claim 1, wherein the at least one pressure sensor is selected from a group comprising: a piezo-resistive pressure sensor, a strain gauge pressure sensor, a mechanical deflection pressure sensor, a vibrating element pressure sensor, or a variable capacitance pressure sensor.

5. An apparatus as in claim 1, further comprising a sample cell to increase an effective path length of light emitted from the at least one light source that is coupled to the light source and the detector, wherein the at least one pressure sensor measures pressure within the sample cell.

6. An apparatus as in claim 1, further comprising: an open path sample cell to increase an effective path length of light emitted from the at least one light source that is coupled to the light source and the at least one detector.

7. An apparatus as in claim 6, wherein the sample cell is chosen from a group comprising: a Herriott cell, a White cell, a cell that has at least one surface reflecting the light emitted from the light source, a cell that has no surface reflecting the light emitted from the light source.

8. An apparatus as in claim 1, further comprising a closed path sample cell to increase an effective path length of light emitted from the at least one light source that is coupled to the light source and the at least one detector.

9. An apparatus as in claim 8, wherein the sample cell is chosen from a group comprising: an on-axis optical resonator having at least one surface reflecting the light emitted from the light source, or an off-axis optical resonator having at least one surface reflecting the light emitted from the light source.

10. An apparatus as in claim 1, wherein the control unit varies the modulation amplitude of the at least one light source according to changes in detected pressure.

11. An apparatus as in claim 1, wherein a shape of the light signal detected by the at least one detector includes a peak and a valley, and wherein the control unit varies the modulation amplitude of the light source to maintain a substantially fixed distance between the peak and the valley.

12. An apparatus as in claim 1, wherein a shape of the light signal detected by the at least one detector includes a peak and a valley, and wherein the control unit varies the modulation amplitude of the light source to maximize a distance between the peak and the valley.

13. An apparatus as in claim 1, wherein a shape of the light signal detected by the detector includes a peak, and wherein the control unit automatically varies the modulation amplitude of the light source to maintain a substantially fixed height of the peak during pressure variations.

14. An apparatus as in claim 1, wherein a shape of the light signal detected by the detector includes a peak, and wherein the control unit automatically varies the modulation amplitude of the light source to maximize a height of the peak during pressure variations.

15. An apparatus as in claim 1, further comprising at least one lock-in amplifier coupled to the at least one detector to isolate a second harmonic component of the detected light.

16. A method of detecting a trace concentration of a target gas within a background gas, the method comprising:
   emitting modulated light at a wavelength substantially corresponding to at least one absorption line of the target gas;
   detecting an intensity of light emitted from the light source that has passed through the target gas at a multiple of a modulation frequency of the emitted light;
   detecting a pressure of the target gas; and
   automatically adjusting a modulation amplitude of the modulated light based on the detected pressure of the target gas.

17. A method as in claim 16, wherein the light is emitted by at least one light source selected from a group comprising: a solid state laser, a tunable diode laser, a quantum cascade laser, a gas laser, a liquid laser, a color center laser, or an optical difference or sum frequency generator.

18. A method as in claim 16, wherein the at least one detector is selected from a group comprising: an InGaAs detector, an hAs detector, a Si detector, a Ge detector, a PbS detector, a Mercury-Cadmium-Telluride detector, or a photomultiplier.

19. A method as in claim 16, wherein the pressure is detected by at least one pressure sensor selected from a group comprising: a piezo-resistive pressure sensor, a strain gauge pressure sensor, a mechanical deflection pressure sensor, a vibrating element pressure sensor, or a variable capacitance pressure sensor.

20. A method as in claim 19, wherein the at least one pressure sensor is mounted in a sample cell to measure the pressure of the target gas.

21. A method as in claim 20, wherein a pressure of the background gas is at least 1 Pa.

22. A method as in claim 16, wherein the concentration of the trace gas is at least 0.01 part per trillion volume of the background gas.

23. A method as in claim 16, wherein the modulation amplitude of the light source is adjusted linearly to the detected pressure.

24. A method as in claim 16, wherein the modulation amplitude of the light source is adjusted non-linearly to the detected pressure.

25. A method as in claim 16, wherein a shape of the detected light signal includes a peak and a valley, and wherein the modulation amplitude of the emitted light is varied to maintain a substantially fixed distance between the peak and the valley.

26. A method as in claim 16, wherein a shape of the detected light signal includes a peak and a valley, and wherein the modulation amplitude of the emitted light is varied to maximize a difference between the peak and the valley.

27. A method as in claim 16, wherein a shape of the detected light includes a peak, and wherein the modulation amplitude of the emitted light is automatically varied to maximize a height of the peak during pressure variations.

28. A method as in claim 16, wherein a shape of the light detected by the detector includes a peak, and wherein the modulation amplitude of the light source is automatically varied to maintain a substantially fixed height of the peak during pressure variations.

29. An apparatus comprising;
   a light source emitting light at a wavelength at which molecules and atoms of a target gas absorb light at a substantially greater level than molecules and atoms of a background gas;
   a detector positioned to detect an intensity of light emitted from the light source;
   at least one pressure sensor to detect a pressure associated with the target gas; and
   a control unit coupled to the detector and the light source to automatically adjust an operating parameter of the light source based on the pressure detected by the at least one pressure sensor.

30. An apparatus as in claim 29, wherein the light source is a tunable diode laser, the tunable diode laser is modulated at a modulation frequency, the detector detects the intensity of light at a multiple of the modulation frequency, the target gas is water, and the background gas is natural gas.

* * * * *